United States Patent [19]

O'Connor

[11] Patent Number: 4,846,179

[45] Date of Patent: Jul. 11, 1989

[54] ELECTRO-MEDICAL METHOD AND APPARATUS FOR TREATING FOLLICULITIS AND CUTANEOUS INFECTED CONDITIONS

[76] Inventor: Edward O'Connor, 10212 Plymouth Ave., Cleveland, Ohio 44125

[21] Appl. No.: 59,334

[22] Filed: Jun. 8, 1987

[51] Int. Cl.$^4$ ................................................ A61N 1/32
[52] U.S. Cl. ................................................ 128/419 R
[58] Field of Search ........... 128/303.1, 303.17, 303.18, 128/303.19, 419 R, 422, 424, 796, 800, 804; 604/20

[56] References Cited

U.S. PATENT DOCUMENTS

| 683,690 | 10/1901 | Johnson | 604/20 |
| 1,603,339 | 10/1926 | Herrmann | 128/424 |
| 2,099,511 | 11/1937 | Caesar | 604/20 |
| 3,994,300 | 11/1976 | Siddons | 128/303.18 |
| 4,572,194 | 2/1986 | Head | 128/419 R |
| 4,667,677 | 5/1987 | Dimino | 128/419 R |

FOREIGN PATENT DOCUMENTS 2035089  6/1980  United Kingdom ............ 128/419 R

Primary Examiner—William E. Kamm

[57] ABSTRACT

A method of treating folliculitis and other cutaneous infected conditions by an electrical spark discharge at the location of the cutaneous lesion, with intensity and duration sufficient to cause inhibition or destruction of the causative infective agent. Significant or permanent damage to the normal tissue or other harmful result is avoided by the utilization of a low discharge power and a short duration of application, as well as by an indirect application of the discharge.

12 Claims, 1 Drawing Sheet

ELECTRO-MEDICAL METHOD AND APPARATUS FOR TREATING FOLLICULITIS AND CUTANEOUS INFECTED CONDITIONS

BACKGROUND OF THE INVENTION

This invention relates to an electro-medical treatment of the type in which a high-frequency alternating current of low power and high tension is applied to an affected site via a non-contacting electrode which serves as one end of a spark gap. Such application of high-frequency alternating current, when utilized for the removal of undesired skin growths, etc., has sometimes been designated in the prior art as fulguration, and has been referred to in numerous publications relating to electro-surgery.

In the prior art, reference has been made to treating skin conditions by using an electrical corona discharge in air to generate ultraviolet radiation. Many references to epilating devices operating on an electrical discharge exist in the prior art. The prior art contains references to corona discharge devices for releiving pain and inducing local immunization by diathermy heat in underlying tissues. Nerve stimulators utilizing an air discharge to a skin-contacting electrode to generate a transcutaneous current pulse exist in the prior art. Dessicating devices for mild destruction of tissue by means of a relatively weak spark are well-known in electrosurgery, as are coagulating devices for producing severe destruction of tissue by means of a strong spark discharge.

Quite surprisingly, in the light of the long history, extensive experimentation, study and evaluation of medically-related electrical discharge devices, it has now been discovered that cutaneous conditions such as pyoderma conditions and fungous conditions of the skin can be rapidly and effectively treated by the use of a properly-generated and controlled electrical spark discharge applied directly to the site of the cutaneous lesion. In spite of the possible trauma and risk of spreading infection known to be associated with disturbance, electrical or otherwise, of an infected site, it has now been realized that an electrical spark applied in accordance with the present invention has been found to produce rapid elimination of the aforementioned cutaneous infection without tissue scarring, epilation or other significant adverse effects. The described treatment is obviously advantageous over conventional antibiotic treatment for rapidity, and avoidance of allergic reaction and other antibiotic side effects. It is also obviously advantageous over such previously-used treatments as UV and x-ray, for reduced risk to the patient, as well as rapidity. Moreover, a new treatment is always advantageous, for it is well-known that no treatment is effective in all cases, particularly when relapsing or chronic, and some cases persist despite all existing treatment.

SUMMARY OF THE INVENTION

While the concept of applying an electrical spark discharge to an affected site to destroy undesired tissue, etc., is well-known in the prior art, in accordance with the present invention such an electric discharge is utilized without significant injury to tissue to effect a treatment of conditions such as folliculitis simplex, furuncle, carbuncle, etc. The above-described utilization for treatment of such conditions is not known in the literature.

Folliculitis simplex is regarded as a pyogenic infection of the hair follicles, often caused by staphylococci. The elementary lesion is regarded as a follicular pustule and the hair bulb itself is usually unaffected. The surrounding skin may be somewhat reddened in this condition but there is no crusting. A furuncle is regarded as a follicular and sebaceous-gland infection. It may be single or multiple. It tends to occur in crops. A patient may have one or two lesions and then be free of involvement or he may have furuncles almost continuously for many months. A furuncle is a solitary boil, and a carbuncle appears as a group of boils run together or as one large boil with several pus pockets.

Since some folliculitis conditions such as furuncles and carbuncles are considered under some conditions to become life-endangering, and to in some cases require hospitalization or even operation, especially those occurring on or about the nose, upper lip, back of neck or beneath the eye, a simple and effective treatment for folliculitis conditions is obviously advantageous.

One object of this invention is to provide a method of treating a folliculitis condition as described above with an electrical spark type of discharge whereby no tissue is significantly injured and no scarring results.

It is another object of this invention to provide a mechanism whereby the effective intensity of the discharge is controllable.

Another object of this invention is to provide a mechanism which ensures against harmful results by utilizing a discharge of very low current.

This method comprises applying the discharge from a suitable non-contacting electrode device to the affected follicle or follicles for one or two seconds, this period of time being sufficient to deactivate, i.e., inhibit or destroy, the causative agent, e.g., bacterial, but insufficient to cause significant tissue damage at the utilized effective intensity of the discharge. A second contact to make a return path for the current is not necessary. The reason, of course, is that at the ringing frequency of the electrode discharge, the capacitance between the patient and the surrounding space and grounded surfaces presents a relatively low impedance. The electrode may be of any desired shape or bluntness, however an electrode of fine diameter may be desirable to restrict the discharge to a small area. The application of the electrical discharge as described results in healing of the follicle site with no permanent loss of hair from the treated follicle, and the treatment is rendered relatively painless by a temporary benumbing effect of the current. During application the discharge tends to jump automatically to the affected follicle because said follicle is usually slightly raised above the surrounding epidermal surface as a result of inflammation consequent to the folliculitis condition. Owing to the low power utilized the spark discharge tends to exhibit a bright yellow appearance, rather than a bluish appearance characteristic of higher power as conventionally associated with fulguration. Since the causative agent of the aforesaid follicle conditions is generally regarded as bacterial, which is a type of infective agent which is considered to be relatively unaffected by current per se, some factor other than current is apparently responsible for deactivation of the causative agent of the folliculitis as a consequence of treatment by the abovedescribed method in accordance with the present invention. Thus, for example, direct contact of the electrode to the skin surface is apparently not found to be efficacious, since with such contact essentially only current flow is produced.

The positioning or moving of the electrode can be accomplished, of course, by hand, or possibly also by machine.

BRIEF DESCRIPTION OF THE DRAWINGS

The sole FIGURE.

DESCRIPTION OF THE PREFERRED EMBODIMENTS

Figure 1:
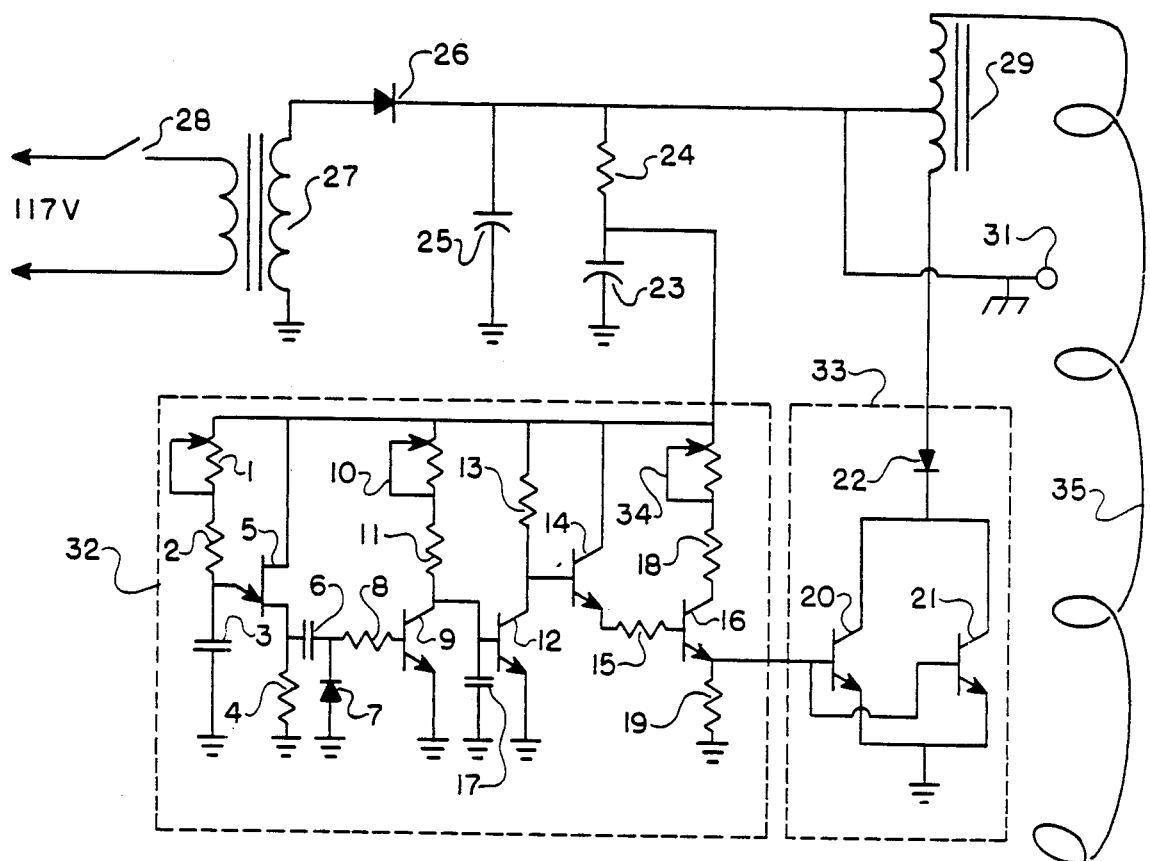
FIG. 1, is a schematic diagram of a circuit suitable for utilization with an electrode device in accordance with the method of the present invention.

The drawing of FIG. 1 illustrates a high-frequency circuit associated with the electrode, with a control circuit for controlling the effective intensity of the discharge, which may be regarded herein as a product of the pulse repetition rate, the pulse duty cycle and the amplitude of the discharge. Indicated schematically is a power transformer 27 in conjuction with a rectifier diode 26 and a filter capacitor 25, for providing B+ to pulsing circuit 32 via decoupling resistor 24 and filter capacitor 23, and to the collector circuit of transformer driver circuit 33. Circuit 33 drives a small Tesla-coil type of transformer, transformer 29, which is connected at the high end of the secondary to a said electrode 30 via an electrode lead 35. Said power transformer 27 is connected to an a.c. line via a switch 28. The lower end of the secondary of transformer 29 is connected to terminal 31 to provide an optional return path, if desired, for the current associated with the spark discharge.

In this embodiment, Tesla transformer driver circuit 33 comprises two power transistors 20 and 21, having bases, collectors and emitters connected in parallel to increase power-handling capability, with the paralleled collectors being connected to the lower end of transformer 29 primary via diode 22. Said driver circuit 33 operates analogously to a mechanical interrupter, alternately grounding and open-circuiting the lower end of said primary of transformer 29. Diode 22 serves to block any reverse flyback voltage from appearing at the collector terminals of transistors 20 and 21.

Pulsing circuit 32 comprises a relaxation oscillator circuit, including unijunction transistor 5, charging capacitor 3, charging potentiometer 1, emitter-current-limiting resistor 2 and base resistor 4; a pulse-stretching circuit, including blocking capacitor 6, discharging diode 7, base-current-limiting resistor 8, discharging transistor 9, charging capacitor 17, charging resistor 10, collector-current-limiting resistor 11, switching transistor 12 and collector resistor 13; and a buffer circuit, including transistors 14 and 16, base-current-limiting resistor 15, emitter resistor 19, drive-current-adjusting potentiometer 34 and drive-current-limiting resistor 18.

The afore-described pulse-stretching circuit operates similarly to a one-shot to extend the width of the output pulse of the afore-described relaxation oscillator circuit, to provide a pulse of optimum duty cycle, said duty cycle being adjustable via potentiometer 10. The pulse frequency is adjustable via potentiometer 1, and is typically about 1 kHz. The base drive level to the afore-mentioned driver circuit 33 is adjustable via potentiometer 34, to adjust the amplitude of, and hence to provide a convenient control of the effective intensity as heretofore defined of, the spark discharge from electrode 30. The spark is typically adjusted for a maximum length of about 1/16", without return path. The maximum spark length obtainable between the electrode 30 and return-path terminal 31 is limited to about ¼" for the application herein disclosed.

While a Tesla device as described is a convenient way to generate an effective electrode voltage waveform, the actual voltage-generating means, of course, is immaterial, and any other means that will produce an equivalent voltage waveform may be utilized to implement this method of treatment.

Of course the above-described circuit is shown in an illustrative, rather than a limiting, sense.

Besides exhibiting usefulness for treating folliculitis conditions as described above, this method of applying an electrical spark discharge may be utilized to ameliorate other cutaneous infected conditions, including, for example, various forms of tinea. For such conditions a more blunt electrode device may be utilized to effect distribution of the discharge over a wider area, and said electrode may also be moved in position so as to effect an overall coverage of an affected zone. However, for such tinea conditions as infected nail conditions, a finer-diameter electrode device may be advantageous to allow improved penetration of the discharge to the keratophilic trichophyton, etc., causative fungal agent, augmented by increased effective intensity.

In most cases, the treatment method according to the present invention may give best results when utilized with a relatively dry cutaneous surface; otherwise a considerable portion of the effect of the electrical spark discharge may be dissipated by conduction associated with surface moisture.

It may be noted that while heat-related sterilizing effects are known to accompany the previously-mentioned method of fulguration, a primary purpose of fulguration is to destroy unwanted tissue, and for this purpose direct electrode contact is often utilized, the destructive effect being substantially attributed to the current; on the other hand a primary purpose of the treatment method according to the present invention is to deactivate a causative infective agent, e.g., bacterial, fungal, etc., which is at least partially protected by the cutaneous tissue, i.e., skin, nails or hair, without significant or permanent damage to said tissue, in a manner not previously known, in which it is advantageous that direct contact not be made since the deactivating effect is apparently not directly attributable to the current.

The foregoing invention can now be practiced by those skilled in the art. From the above, it will be seen that the treatment method according to the present invention is capable of use in a variety of situations.

In general, it will be understood that changes in the details herein described and illustrated for the purpose of explaining the nature of the invention may be made by those skilled in the art, without departing from the spirit and scope of the invention as expressed in the appended claims. It is, therefore, intended that these details be interpreted as illustrative, and not in a limiting sense.

I claim:

1. A method of treating a cutaneous infected condition comprising the steps of:
    (a) bringing an electrode into proximity with an infected cutaneous portion so as to form a arcable gap between the electrode and the affected said portion;
    (b) supplying high-frequency electrical energy to the electrode so causing a spark discharge between the electrode and the infected cutaneous portion; and
    (c) controlling a duration and an effective intensity of said spark discharge so as to cause a spark discharge sufficient to cause deactivation of an infective agent in the infected cutaneous portion but insufficient to cause significant damage to normal tissue in said affected portion.

2. The method according to claim 1, wherein said spark discharge comprises pulsed electrical energy, comprising utilizing means for adjusting pulse repetition rate, pulse duration and pulse amplitude of said discharge to control said effective intensity of said discharge.

3. The method according to claim 2, wherein said cutaneous infected condition is a folliculitis simplex condition, and wherein said causing step includes causing said, discharge to pass between said electrode and at least one selected hair follicle.

4. The method according to claim 2, wherein said cutaneous infected condition is a furuncular condition, and wherein said causing step includes causing said discharge to pass between said electrode and a hair follicle of at least one involved furuncle.

5. The method according to claim 2, wherein said cutaneous infected condition is a carbuncular condition, and wherein said causing step includes causing said, discharge to pass between said electrode and at least one selected hair follicle of an involved carbuncle.

6. The method according to claim 2, wherein said cutaneous infected condition is a tinea condition, and wherein the position of said electrode is varied by moving said electrode over an entire surface of said affected portion in such a manner as to effect overall coverage of said affected portion by said discharge.

7. The method according to claim 2, wherein said infected cutaneous condition is a tinea infected nail condition, and wherein the position of said electrode is varied by moving said electrode over an entire surface of said affected portion in such a manner as to effect overall coverage of said affected portion by said discharge.

8. The method according to claim 1, wherein said cutaneous infected condition is a folliculitis simplex condition, and wherein said causing step includes causing said, discharge to pass between said electrode and at least one selected hair follicle.

9. The method according to claim 1, wherein said cutaneous infected condition is a furuncular condition, and wherein said causing step includes causing said, discharge to pass between said electrode and a hair follicle of at least one involved furuncle.

10. The method according to claim 1, wherein said cutaneous infected condition is a carbuncular condition, and wherein said causing step includes causing said, discharge to pass between said electrode and at least one selected hair follicle of an involved carbuncle.

11. The method according to claim 1, wherein said cutaneous infected condition is a tinea condition, and wherein the position of said electrode is varied by moving said electrode over an entire surface of said affected portion in such a manner as to effect overall coverage of said affected portion by said discharge.

12. The method according to claim 1, wherein said infected cutaneous condition is a tinea infected nail condition, and wherein the position of said electrode is varied by moving said electrode over an entire surface of said affected portion in such a manner as to effect overall coverage of said affected portion by said discharge.

* * * * *

UNITED STATES PATENT AND TRADEMARK OFFICE
CERTIFICATE OF CORRECTION

PATENT NO. : 4,846,179

DATED : July 11, 1989

INVENTOR(S) : Edward O'Connor

It is certified that error appears in the above-identified patent and that said Letters Patent is hereby corrected as shown below:

Column 4, after line 28 and before line 29, insert the following:
--Referring again to the drawing, Fig. 1, an example body portion 36 is indicated, although the method and apparatus disclosed herein applies to any body portion. An example electrode 30 is shown in three example alternate positions, at example lesions L1, L3 and L4 of portion 36, which also exhibits an example lesion L2. Example stray capacitances forming a current return path from said portion 36 to "earth" ground, i.e., the tap of induction coil 29, in the example apparatus of Fig. 1, are also indicated, for a monoterminal case wherein return path terminal 31 is not connected directly to the body, although the method may be carried out with the terminal so connected if desired. An example sequence of application of the spark discharge S is indicated by arrows and dotted line as beginning at L1, moving to L2, from there to L3 and then to L4. Of course, the order of application may be in any sequence, and there may be various numbers, sizes or types of infected lesions, of this or other body portions (not shown). The length of the spark is exaggerated for clarity in the drawing; a short spark as heretofore mentioned in the disclosure is often preferable, although grosser lesions may require a longer spark; however, even direct contact, although apparently inefficacious if such contact results only in current flow, and generally to be held to a minimum since it tends to interrupt the spark, may in some cases support spark discharge with partially-insulating tissue, as, e.g., nail. At L1 an example tip 30A1, being a tip of, e.g., relatively fine diameter, to assist in restricting the discharge to a small area, is utilized, L1 being representative from its outline of a small lesion such as, e.g., folliculitis, dermatophytid (associated with tinea spores), small furuncle, acne vulgaris lesion (if on, e.g., face or trunk, not shown), etc. After directing the spark to the lesion by positioning the electrode proximal to the lesion and allowing the spark

UNITED STATES PATENT AND TRADEMARK OFFICE
CERTIFICATE OF CORRECTION

PATENT NO. : 4,846,179

DATED : July 11, 1989

INVENTOR(S) : Edward O'Connor

It is certified that error appears in the above-identified patent and that said Letters Patent is hereby corrected as shown below:

to jump, as described previously in the disclosure, the electrode probe 30 may be moved to, for example, L2, as indicated by the arrow connecting L1 to L2, and the spark may be similarly directed to that lesion, using, e.g., the same tip, L2 being representative of from its outline, in this example, a lesion similar to L1. The electrode probe may then be moved, for example, to L3, as indicated by the arrow connecting L2 to L3, after, for example, changing tip 30A1 to tip 30A3, which is indicated in the drawing as, e.g., a loop- or ball-shaped, i.e., more blunt, tip, to assist in distribution of the discharge over a larger area, and the spark may be guided over the surface of L3, which is representative from its outline of an extended lesion of a more substantially sized affected portion, such as, e.g., dermatophytosis (tinea), carbuncle, ulcerative tinea, mixed-infection or other ulcerative infected lesion, etc., by positioning the electrode proximal the surface at, for example, the tip of the previously-mentioned arrow and then moving the electrode over the lesion surface by, for example, scanning path SP3, to effect overall or substantially overall coverage. Particularly where L3 is ulcerative, for example, the perimeter can also be scanned (not shown). Where L3 is, e.g., carbuncular, the electrode can also be positioned proximal to one or more central necrotic areas (not shown) characteristic of such a lesion, and if such carbuncular, furuncular, etc., central areas exhibit significant opening due to advanced state, the tip can be directly inserted, and shorting can be prevented if, e.g., insulating material of the probe 30 extends over or slightly past the conductive tip. The tip or carrier can of course be made thinner for such purpose and a spark can jump from recess in such carrier to the infected tissue. The electrode probe may then be moved, for example, to L4, as indicated by the arrow connecting L3 to L4, after, for example, changing tip 30A3 to tip 30A4, a tip of, e.g., relatively fine diameter, to assist in this exam-

UNITED STATES PATENT AND TRADEMARK OFFICE
CERTIFICATE OF CORRECTION

PATENT NO. : 4,846,179

DATED : July 11, 1989

INVENTOR(S) : Edward O'Connor

It is certified that error appears in the above-identified patent and that said Letters Patent is hereby corrected as shown below:

ple in effecting penetration of the discharge into hard material such as nail, and the spark may be guided over the surface of L4, which from its outline is representative of, e.g., nail plate lesion such as onychomycosis (tinea infected nail), by positioning the electrode proximal to the surface of L4 at, for example, the tip of the previously-mentioned arrow and then moving the electrode over the lesion surface by, for example, scanning path SP4, possibly in direct contact, moving the electrode slowly enough not to extinguish the spark, but rapidly enough not to produce undue thermal effects on the nail bed, to effect overall or substantially overall coverage of discolored, cracked or partially-separated areas characteristic of such a nail plate lesion. The electrode may then be moved if desired to other lesions, of the same or other portions of the body, and at each lesion, which may be external or in some cases internal (not shown), the electrode device may be changed and effective intensity adjusted as required.--

Column 4, after line 43 and before line 44, insert the following:
--Upon the application of a spark discharge as heretofore set forth, to deactivate or disable an infective agent or agents, rather than to primarily remove tissue, various effects, such as ion bombardment, heat, drying and other simultaneous, direct and indirect, physical, chemical and biological effects, as well as an associated electrical current, occur, tending to result in suppression of one or more infective agents, according to the amount of effective intensity and duration of application of the discharge. The effective intensity of the discharge, as heretofore set forth in the disclosure, is regarded as an expression for the disabling effect of the discharge on the bacterial, fungal or other infective agent, and has been defined as a product or function of the defined energy content of the discharge,

UNITED STATES PATENT AND TRADEMARK OFFICE
CERTIFICATE OF CORRECTION

PATENT NO. : 4,846,179

DATED : July 11, 1989

INVENTOR(S) : Edward O'Connor

It is certified that error appears in the above-identified patent and that said Letters Patent is hereby corrected as shown below:

namely, an intensity average of the amplitude of the discharge, the pulse duty cycle of a repetitively pulsed discharge, and the pulse repetition rate of such a discharge. In regard to determining what effective intensity would be sufficient for deactivating microbial or other infective agents but insufficient to cause significant tissular damage, i.e., a combination of the above-mentioned factors to provide useful disablement of the infection, it may be noted that the higher the amplitude component, or current after sparking potential has been reached, of the spark discharge, the larger the cross-section of the ionized gas conducting the current, and the more intensely it is ionized. The spark jumps when the electric field between the electrode and tissue becomes sufficient to produce the sparking potential, which depends, as is known, on separation of electrode and, e.g., tissue, type of gas, e.g., air, and pressure of gas, and the maximum gap the spark will jump establishes an amplitude range as, e.g., heretofore set forth in the disclosure. Utilizing a relatively high value of a pulse rate component of the energy content of the discharge, as, e.g., previously set forth as an example in the disclosure, enables applying a high amplitude of spark discharge to an infective agent, thus tending to provide, e.g., a large amount of instantaneous ion bombardment, known to be deleterious to microbial organisms, while reducing tissue-disruptive thermal effects, which might otherwise occur due to excessively rapid discharge-period temperature rise if a continuous or low-rate on-off type of discharge, having the same amplitude, was used; controlling the pulse duty cycle component of the energy content of the discharge, while not critical, further assists in controlling such thermal effects, since the lower the duty cycle, the slower the temperature rise at point of application for the same amplitude, thus allowing more controlled application of the discharge to the lesion. It may also be noted that utilizing a pulse rate in such a range as, e.g., previously disclosed, may in

UNITED STATES PATENT AND TRADEMARK OFFICE
CERTIFICATE OF CORRECTION

PATENT NO. : 4,846,179

DATED : July 11, 1989

INVENTOR(S) : Edward O'Connor

It is certified that error appears in the above-identified patent and that said Letters Patent is hereby corrected as shown below:

some cases provide additional mechanical disruptive effects on microbial organisms, since sonic shock waves are produced by a repetitively pulsed spark discharge, and such organisms are known to be sonically or ultrasonically disruptible.

Because the amplitude-associated thermal effects of the spark are superficial, in contrast to, e.g., treatment of tumors by fulguration, electrodessication, electrocoagulation, etc., wherein all abnormal or diseased cells, and even, in some cases, an extensive zone of cells surrounding the tumor zone, must be removed or killed by heating, such effects being particularly superficial in a monoterminal mode wherein return path terminal 31 of the example therapeutic apparatus of Fig. 1 is not connected to the body, tissues which had been affected but not necrotized by an infective agent or agents remain primarily intact and viable; and fibrous reaction, during healing of tissues, is suppressed, since tissue injury limited to the epidermis is known to heal without scar by outgrowth of sheets from the normal epithelium, so that the new skin cannot be differentiated from the old, resulting in substantial or complete absence of scar formation.

Dosage in local treatments often tends to depend on the skill or experience of an individual practitioner, because of uncertainties of exact dosage arising from factors such as chronicity of causative agent, superficiality or depth of problem zone, state of advancement of lesion, species in the case of non-human lesions, etc.; however, treatment in accordance with the disclosed method, utilizing apparatus of a type disclosed, tends to be relatively non-critical, in comparison to modalities such as, e.g., phototherapy or superficial x-ray, which tend to frequently provoke precancerous conditions such as radiodermatitis.--

UNITED STATES PATENT AND TRADEMARK OFFICE
CERTIFICATE OF CORRECTION

PATENT NO.   : 4,846,179
DATED        : July 11, 1989
INVENTOR(S)  : Edward O'Connor It is certified that error appears in the above-identified patent and that said Letters Patent is hereby corrected as shown below:

Column 2, line 64, "abovedescribed" should read --above-described--.
Column 5, line 13, "ing said," should read --ing said--.
Column 5, line 22, "causing said," should read --causing said--.
Column 6, line 8, "ing said," should read --ing said--.
Column 6, line 12, "causing said," should read --causing said--.
Column 6, line 17, "causing said," should read --causing said--.

Signed and Sealed this

Tenth Day of July, 1990

*Attest:*

HARRY F. MANBECK, JR.

*Attesting Officer*     *Commissioner of Patents and Trademarks*